United States Patent

Springer et al.

[11] Patent Number: 4,659,856
[45] Date of Patent: Apr. 21, 1987

[54] 4,4'-BIS-(β-HYDROXYETHYLSULFONYL)-BIPHENYL AND ITS ESTERS

[75] Inventors: Hartmut Springer, Königstein; Gerd König, Hofheim am Taunus, Fed. Rep. of Germany

[73] Assignee: Hoechst Aktiengesellschaft, Fed. Rep. of Germany

[21] Appl. No.: 775,138

[22] Filed: Sep. 12, 1985

[30] Foreign Application Priority Data

Sep. 15, 1984 [DE] Fed. Rep. of Germany ....... 3433981

[51] Int. Cl.$^4$ ................. C07C 141/18; C07C 147/10; C07C 69/017; C07F 9/145
[52] U.S. Cl. ...................................... 558/26; 558/162; 558/33; 558/184; 560/308; 568/32; 8/516; 8/517
[58] Field of Search ...................... 568/32; 558/26, 33, 558/162, 184; 560/308

[56] References Cited

U.S. PATENT DOCUMENTS

Re. 26,792  2/1970  Tesoro ................................. 558/26
3,218,118  11/1965  Steele et al. ........................ 568/32

Primary Examiner—Nicky Chan
Attorney, Agent, or Firm—Connolly and Hutz

[57] ABSTRACT

Compounds of the general formula (1)

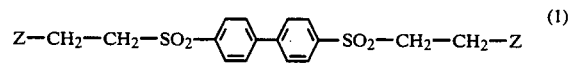

in which the Zs, preferably identical to each other, each denote a hydroxy group or a sulfato, thiosulfato or phosphato group. They can be prepared by first converting biphenyl by sulfochlorination into biphenyl-4,4'-disulfochloride, then reducing the latter with an alkali metal or alkaline earth metal sulfite or hydrogensulfite to sulfinic acid, and in turn reacting the latter with ethylene oxide to give 4,4'-bis-(β-hydroxyethylsulfonyl)-biphenyl, which can be esterified in conventional manner. They are used for modifying and improving the physical and coloristic properties of materials made of natural and/or synthetic polyamide fibers and/or polyurethane fibers and as auxiliaries in dyeing processes for such fiber materials.

3 Claims, No Drawings

4,4'-BIS-(β-HYDROXYETHYLSULFONYL)-BIPHENYL AND ITS ESTERS

The present invention provides new compounds which are suitable for modifying and improving the properties of wool and of other carboxamido-containing materials. The new compounds have the general formula (1)

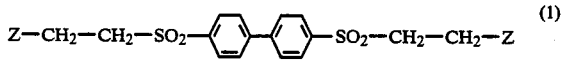

in which both Z preferably have the same meaning as each other and each is a hydroxy group or a sulfato group (of the general formula —$OSO_3M$, in which M stands for a hydrogen atom or an alkali metal, such as sodium, potassium, lithium, or one equivalent of an alkaline earth metal, such as calcium) or a thiosulfato group (of the general formula —S—$SO_3M$ with M of the abovementioned meaning) or a phosphato group (of the general formula —$OPO_3M_2$ with M of the abovementioned meaning). Compounds of the general formula (1) according to the invention in which one or both Z stand for a hydroxy group serve as precursors in the preparation of compounds (1) according to the invention in which the Zs are each a sulfato, thiosulfato or phosphato group.

Preference is given to those compounds according to the invention in which one or preferably both Z denote a sulfato group.

The present invention also relates to a process for preparing these compounds of the general formula (1). This process comprises sulfochlorinating biphenyl, reacting the biphenyl-4,4'-disulfochloride with an aqueous solution of an alkali metal or alkaline earth metal hydrogensulfite or sulfite and thus converting the sulfochloride groups into sulfino groups or their alkali metal salts or alkaline earth metal salts, then converting the two sulfino groups with ethylene oxide to β-hydroxyethylsulfonyl groups, and reacting the 4,4'-bis-(β-hydroxyethylsulfonyl)-biphenyl, if desired for preparing its sulfate or phosphate half-ester (sulfato or phosphato compounds), with a sulfating or phosphating agent, and if desired to prepare the thiosulfato compounds of the formula (1), reacting the sulfato compound of the formula (1) in which Z(s) stand(s) for sulfato group(s) with an alkali metal thiosulfate salt in aqueous solution in initially an alkaline and then a weakly acid range.

The methods of sulfochlorination, of reducing to the sulfino group, of ethoxylation, of sulfation and of phosphation and of converting β-sulfatoethylsulfonyl groups into β-thiosulfatoethylsulfonyl groups are known per se. The reactions according to the invention can be carried out analogously to such procedures described in the literature.

The sulfochlorination is effected for example with chlorosulfonic acid or monohydrate and thionyl chloride; it can be carried out analogously to a procedure as described for example in Houben-Weyl, Methoden der Organischen Chemie [Methods of Organic Chemistry], Volume IX, page 578 (1955), where the reaction is preferably carried out at a temperature between 40° and 100° C., in particular between 60° and 70° C.

The biphenyl-4,4'-disulfochloride, for example analogously to Houben-Weyl, loc. cit., page 306, is then reduced preferably by means of an alkali metal sulfite or alkali metal hydrogen-sulfite, in particular sodium sulfite or sodium hydrogen-sulfite, in the presence of an alkali metal carbonate or alkali metal hydroxide, such as sodium carbonate or sodium hydroxide, in aqueous solution, preferably at a temperature between 0° C. and 80° C., in particular between 60° and 70° C., and at a pH between 7.0 and 10.0, preferably between 8.0 and 8.5, to the corresponding biphenyl-4,4'-disulfinic acid. This acid is then converted with ethylene oxide in the presence of aqueous sulfuric acid or phosphoric acid, for example analogously to the procedure described in U.S. Pat. No. 3,647,813, at a temperature between 30° and 70° C., preferably between 50° and 60° C., and at a pH between 4.5 and 9.0, in particular between 7.0 and 8.0, to give the compound of the general formula (1) according to the invention in which both the Z stand for a hydroxy group, i.e. to 4,4'-bis-(β-hydroxyethylsulfonyl)-biphenyl.

The esterification of the β-hydroxyethylsulfonyl compound into its sulfato or phosphato derivatives can be effected analogously to procedures as described for example in German Auslegeschriften Nos. 1,248,188, 1,256,542 and 1,443,877 on the one hand and in German Auslegeschrift No. 1,795,086 on the other. The sulfating agent used can be for example 98–100% strength sulfuric acid, sulfuric acid containing sulfur trioxide, chlorosulfonic acid. or sulfamic acid in the presence of pyridine. The phosphating agent used can be phosphoric acid or polyphosphoric acid or solutions of phosphorus pentoxide in phosphoric acid or polyphosphoric acid. For instance, to prepare the β-sulfatoethylsulfonyl compound according to the invention from the corresponding β-hydroxyethylsulfonyl compound, this hydroxy compound can be sulfated with 98–100% strength sulfuric acid or sulfuric acid containing up to about 30% by weight of sulfur trioxide at a temperature between −5° C. and +50° C., preferably between 20° and 25° C. The sulfato compound formed can be precipitated at room temperature or a lower temperature from its acid solution diluted with ice and be isolated; the acid compound obtained can then be converted in conventional manner by means of an alkali metal hydroxide, alkali metal carbonate or alkali metal hydrogencarbonate or an alkaline earth metal hydroxide or carbonate into its salts and be isolated from the aqueous medium by spray drying.

The conversion of the hydroxyethylsulfonyl compound according to the invention into its β-phosphatoethylsulfonyl derivatives is effected with the stated phosphating agents for example at a temperature between 20° and 120° C., preferably at a temperature between 95° and 100° C. Like the acid sulfato compounds, the acid phosphato compounds can be converted into their salts and isolated.

The thiosulfato compounds according to the invention can be prepared for example analogously to the procedures as described for example in German Patent No. 1,246,906. Thus the preferred way of preparing the thiosulfato compounds according to the invention is by converting the corresponding sulfato compound according to the invention in aqueous solution by means of an alkali metal hydroxide or carbonate at a pH between 10 and 13, preferably between 11.5 and 12.3, and at a temperature between 20° and 80° C., preferably between 35° and 45° C., into the corresponding vinylsulfonyl compound. The aqueous solution or suspension of the vinylsulfonyl compound is then reacted with an alkali metal thiosulfate, preferably sodium thiosulfate, at a temperature between 40° and 90° C., preferably between 70° and 75° C., and at a pH between 4.5 and 7.5, preferably between 5.7 and 6.2, to give the solution of the β-thiosulfatoethylsulfonyl compound. The thiosulfato compound can be precipitated from the aqueous solution by addition of alkali metal halides, preferably potassium chloride, and be isolated.

The new compounds of the general formula (1) serve for modifying and improving the physical and dyeing properties of materials made of natural and/or synthetic polyamide fibers, such as wool, polyamide-6, polyamide-6,6 and -11, and/or polyurethane fibers and as useful auxiliaries in dyeing processes for such materials. Thus they improve for example the levelness of polyamide dyeings if, before the actual dyeing process or together with the dyestuff during the dyeing process, they are allowed to act on the natural and/or synthetic polyamide fiber. It is similarly possible to improve for example the wet tear strength of wool by treatment with the new compounds of the formula (1). It is also possible to reduce the loss of fiber which customarily occurs on dyeing wool at the boil by means of the new compounds of the formula (1). This is because in the dyeing of wool, owing to the dyeing conditions, some of the wool is destroyed by hydrolysis, as is manifested in reduced fiber strength and in increased alkali solubility of the wool. The same is true to a certain extent of polyamide and polyurethane fiber materials. The treatment of wool and of these synthetic materials with a compound according to the invention in an aqueous bath has the effect, however, that the resistance of wool and similarly of the other carboxamido-containing fibers to the requisite dyeing conditions is considerably improved. The loss of strength after the dyeing is reduced in the same way as the alkali solubility. Furthermore, there is an improvement in the wet fastness properties of the resulting dyeings. The material is treated for example by treating the wool fabric or wool fiber before the dyeing process or during the same together with the dyestuff, for example an acid dyestuff or a reactive dyestuff, with a compound of the formula (1) dissolved in a liquor or in the stated dyeing liquor itself. The action of the compounds of the general formula (1) on these fiber materials can be effected analogously to the process conditions and procedures as are commonly customarily and in known manner used for dyeing these fiber materials by means of fiber-reactive dyestuffs (see for example page 15 lines 27 et seq. to page 16 line 9, and page 16 lines 23 et seq. to page 17 line 23 of German Offenlegungsschrift No. 3,132,917).

The following examples serve to illustrate the invention. The parts and percentages are by weight unless otherwise stated. Parts by weight relate to parts by volume as the kilogram relates to the liter.

EXAMPLE 1

(a) 154 parts of biphenyl are added at a temperature of about 30° C. with thorough stirring to 760 parts of 100% strength sulfuric acid in the course of about 90 minutes. The batch is then stirred between 45° and 50° C. for approximately a further hour and then at 75° C. for a further 2 hours. 1,000 parts of thionyl chloride are then gradually added at a temperature of 65° to 70° C. in the course of about 15 hours. At the end of this reaction the reaction mixture is cooled down to 40° to 45° C., and the suspension is stirred into 2,400 parts of ice. 250 parts of sodium chloride are added, and the temperature is maintained at 10° C. After further stirring for about 90 minutes the precipitated product is filtered off with suction, is washed with a total of 1,300 parts of water and is sucked dry on a filter press. Yield: 333 parts corresponding to 95% of theory; melting point: 203° C.

(b) The biphenyl-4,4'-disulfochloride obtained in (a) is reduced to the sulfinic acid compound. To this end, a solution is prepared from 325 parts of 40% strength aqueous sodium sulfite solution and 280 parts of aqueous 33% strength sodium hydroxide solution in 1,660 parts of water. The biphenyldisulfochloride obtained in (a) is added with thorough stirring a little at a time to this hot solution at 80° C. and adjusted to pH 8 with sodium hydroxide solution in the course of about 90 minutes, during which the pH is maintained at a value of 8 by gradual addition of about 430 parts of 33% strength aqueous sodium hydroxide solution. After stirring at this temperature for approximately a further hour and then cooling down to 20° C., the sodium biphenyldisulfinate precipitated in crystalline form is filtered off with suction and dried. Yield: about 318 parts.

(c) The biphenyldisulfinate obtained in (b) is dissolved at a pH between 8.1 and 8.3 and at a temperature of about 60° C. in 2,500 parts of water. While maintaining this temperature and this pH range, 132 parts of ethylene oxide are passed into the solution in the course of about 3 hours; this pH range is maintained by means of 20% strength aqueous phosphoric acid; the pH range is also maintained during the subsequent stirring for 2 hours (a total of about 380 parts of 20% strength aqueous phosphoric acid are consumed).

The 4,4'-bis-(β-hydroxyethylsulfonyl)-biphenyl formed in c) precipitates quantitatively during the ethoxylation reaction. After cooling down the reaction batch to 20° to 30° C. the product is filtered off with suction and washed with water.

Yield: 304 parts corresponding to 82% of theory, relative to starting biphenyl;

Melting point: 197° C.; purity by analysis: greater than 98%.

Analysis:
Calculated: C 51.8%; H 4.8%; S 17.2%;
Found: C 51.3%; H 4.8%; S 17.3%.

EXAMPLE 2

370 parts of 4,4'-bis-(β-hydroxyethylsulfonyl)-biphenyl are added at initially 0° to 5° C., later at at most 30° C., to 1,800 parts of 100% strength sulfuric acid in the course of 2 hours. The batch is subsequently stirred for 12 hours and is then stirred into 10,000 parts of ice-water. A pH of 5 is set by means of about 1,700 parts of calcium carbonate, the calcium sulfate formed is filtered off with suction and washed with 3,000 parts of water. 600 parts of potassium chloride are added to the filtrate, and the 4,4'-bis-(β-sulfatoethylsulfonyl)-biphenyl compound according to the invention thus salted out is filtered off with suction and is dried at 30° to 60° C. under reduced pressure.

The result obtained is a colorless product which contains potassium chloride and a little potassium sulfate and which contains 450 parts of the sulfato compound according to the invention in the form of its potassium salt.

The compound according to the invention can be used to improve the wet tear strength of wool and similarly the wet fastness properties of dyeings on wool obtained with dyestuffs by pretreating this material in accordance with the invention in an aqueous bath containing the compound according to the invention or by adding this compound according to the invention to a dyebath, containing the dyestuff, for wool (cf. also Example 5 below).

EXAMPLE 3

To prepare the 4,4-bis-(β-phosphatoethylsulfonyl)-biphenyl compound according to the invention, 370 parts of 4,4'-bis-(β-hydroxyethylsulfonyl)-biphenyl are added with thorough stirring to a hot mixture at 100° C. of 600 parts of a polyphosphoric acid which is 84% strength in phosphorus pentoxide and 108 parts of 80% strength aqueous phosphoric acid in the course of 15 minutes. The resulting melt is stirred at 100° C. for a further 2 hours, and then, without cooling down, 1,400 parts of water are added in such a way that the temperature should not drop below 80° C. The resulting solution is refluxed for about 30 minutes and is then stirred for a number of hours until cold. 100 parts of potassium chloride are added to the solution, and stirring is continued for a further 2 hours.

The salted-out 4,4'-bis-(β-phosphatoethylsulfonyl)-biphenyl compound according to the invention is filtered off with suction and is maintained at 30° to 60° C. under reduced pressure. This gives a colorless electrolyte-containing (preferably potassium chloride) product which contains 500 parts of the phosphato compound according to the invention in the form of its potassium salt.

The compound according to the invention can be used to improve the wet tear strength of wool and similarly the wet fastness properties of dyeings obtained on wool with dyestuffs by pretreating this material in accordance with the invention in an aqueous bath containing the compound according to the invention or by adding this compound according to the invention to a dyebath, containing the dyestuff, for wool; the procedure adopted can be analogous to Example 5 below.

EXAMPLE 4

To prepare the 4,4'-bis-(β-thiosulfatoethylsulfonyl)-biphenyl compound according to the invention, 545 parts of 4,4'-bis-(β-sulfatoethylsulfonyl)-biphenyl are dissolved in 4,000 parts of water; the solution is warmed to 40° C., and 800 parts of 20% strength aqueous sodium hydroxide solution are added with stirring in the course of 15 minutes. The solution is then stirred at 40° C. for a further 30 minutes, and 750 parts of sodium thiosulfate containing water of crystallization are then added, the solution is heated to 70° to 75° C. and is brought by means of 50% strength aqueous acetic acid to a pH between 5.7 and 6.2. This pH range is maintained for a further 3 hours by means of further aqueous acetic acid.

The thiosulfato compound according to the invention is salted out by addition of 600 parts of potassium chloride and is isolated. The result obtained is 480 parts of an electrolyte-containing powder (preferably potassium chloride) which contains 300 parts (corresponding to a yield of 55% of theory) of the potassium salt of 4,4'-bis-(β-thiosulfatoethylsulfonyl)-biphenyl.

The compound according to the invention undergoes gradual decomposition on heating to above 200° C.

The compound according to the invention can be used to improve the wet tear strength of wool and similarly the wet fastness properties of dyeings obtained on wool with dyestuffs by pretreating this material in accordance with the invention in an aqueous bath containing the compound according to the invention or by adding this compound according to the invention to a dyebath, containing the dyestuff, for wool; the procedure adopted can be analogous to Example 5 below.

EXAMPLE 5

(Application)

(a) 100 g of wool yarn were first dyed for 30 minutes at 100° C. in 2 liters of an aqueous bath which contained 2 g of the acid dyestuff with the Colour Index name C.I. Acid Violet 9 (C.I. No. 45,190) as well as 2 g of sulfuric acid and 10 g of sodium sulfate. 3 g of the compound according to the invention 4,4'-bis-(β-sulfatoethylsulfonyl)-biphenyl were then added in the form of the sodium salt, the dyebath was brought to pH 5, and the dyeing process was continued at 100° C. for a further 60 minutes. The dyed fabric was subsequently removed from the bath, was thoroughly rinsed with warm and cold water, and was then dried.

The dyed wool yarn was tested for color fastness in the wash according to DIN 54,010. The shade of the wool yarn underwent a color change corresponding to an assessment of 4.

(b) 100 g of wool yarn were dyed at 100° C. in 2 liters of an aqueous bath which contained 2 g of the acid dyestuff C.I. Acid Violet 9 (C.I. No. 45,190) as well as 2 g of sulfuric acid and 10 g of sodium sulfate for 60 minutes. The dyed fabric was then removed from the bath, was thoroughly rinsed with warm and cold water and was then dried. The dyed wool yarn was examined for color fastness in the wash according to DIN 54,010. The hue of the wool yarn underwent a color change corresponding to an assessment of 2.

We claim:

1. A compound of the formula

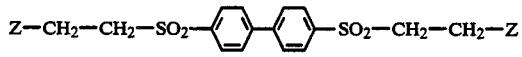

in which the radicals Z, which are identical to one another, each denotes a hydroxy group or a sulfato, thiosulfato or phosphato group.

2. A compound as claimed in claim 1, in which each Z denotes a sulfato, thiosulfato or phosphato group.

3. A compound as claimed in claim 1, in which each Z is a sulfato group.

* * * * *